(12) United States Patent
Graf et al.

(10) Patent No.: US 10,736,650 B2
(45) Date of Patent: Aug. 11, 2020

(54) DEVICE FOR RECEIVING A PREPARATION IN AN EXTRACTION BAG

(71) Applicant: BOWA-electronic GmbH & Co. KG, Gomaringen (DE)

(72) Inventors: Thomas Graf, Gomaringen (DE); Ingo Kiessling, Ofterdingen (DE); Karl-Guenter Noe, Cologne (DE); Michael Anapolski, Duesseldorf (DE)

(73) Assignee: BOWA-electronic GmbH & Co. KG (DE)

( * ) Notice: Subject to any disclaimer, the term of this patent is extended or adjusted under 35 U.S.C. 154(b) by 87 days.

(21) Appl. No.: 15/770,916

(22) PCT Filed: Oct. 31, 2016

(86) PCT No.: PCT/EP2016/076233
§ 371 (c)(1),
(2) Date: Apr. 25, 2018

(87) PCT Pub. No.: WO2017/072359
PCT Pub. Date: May 4, 2017

(65) Prior Publication Data
US 2018/0303511 A1    Oct. 25, 2018

(30) Foreign Application Priority Data

Oct. 29, 2015   (DE) .................. 10 2015 118 545
Nov. 11, 2015   (DE) .................. 10 2015 119 427

(51) Int. Cl.
*A61B 17/3205*    (2006.01)
*A61B 17/00*      (2006.01)
(Continued)

(52) U.S. Cl.
CPC .. *A61B 17/32056* (2013.01); *A61B 17/00234* (2013.01); *A61B 18/1402* (2013.01);
(Continued)

(58) Field of Classification Search
CPC ........ A61B 17/00234; A61B 17/32056; A61B 18/1402; A61B 18/1482;
(Continued)

(56) References Cited

U.S. PATENT DOCUMENTS 5,190,542 A    3/1993  Nakao et al.
5,618,296 A    4/1997  Sorensen et al.
(Continued)

FOREIGN PATENT DOCUMENTS

DE    197 30 525 A1    1/1999
DE    10328329         1/2005
(Continued)

OTHER PUBLICATIONS

Translation of International Preliminary Report on Patentability for International Application No. PCT/EP2016/076233 dated May 11, 2018.
(Continued)

*Primary Examiner* — Jocelin C Tanner
(74) *Attorney, Agent, or Firm* — Gerald E. Hespos; Michael J. Porco; Matthew T. Hespos

(57) ABSTRACT

A device (1) has an extraction bag (5) to receive a preparation (29) that is detached using an electrosurgical cutting loop (6, 6') in a body cavity (27). The extraction bag (5) can be extended out of a distal opening (10) of an insertion tube (3). The cutting loop (6, 6') is flexible and can be extended out of the insertion tube (3) together with the extraction bag (5). The cutting loop (6, 6') is adjacent a first bag opening (9) and adjacent a first loop (8'). The cutting loop (6, 6') has an exposed non-insulated electrically conductive cutting region (14, 14') at the distal end (13, 13') of the loop, and an insulated region (15, 15') outside of the cutting region (14,
(Continued)

14'). The extraction bag (5) has at least one second closable bag opening (17) at the end facing away from the first bag opening (9).

15 Claims, 4 Drawing Sheets

(51) Int. Cl.
    *A61B 18/14*     (2006.01)
    *A61B 18/00*     (2006.01)
(52) U.S. Cl.
    CPC .............. *A61B 18/1482* (2013.01); *A61B 2017/00287* (2013.01); *A61B 2017/00353* (2013.01); *A61B 2017/00358* (2013.01); *A61B 2017/00929* (2013.01); *A61B 2018/00601* (2013.01); *A61B 2018/141* (2013.01); *A61B 2018/1475* (2013.01)
(58) Field of Classification Search
    CPC .......... A61B 2017/00287; A61B 2017/00353; A61B 2017/00358; A61B 2017/00929; A61B 2018/00601; A61B 2018/141; A61B 2018/1475
    See application file for complete search history.

(56) References Cited

U.S. PATENT DOCUMENTS

| | | | |
|---|---|---|---|
| 5,741,271 A * | 4/1998 | Nakao | A61B 1/015 604/523 |
| 5,788,709 A | 8/1998 | Riek et al. | |
| 5,895,392 A | 4/1999 | Riek et al. | |
| 5,971,994 A | 10/1999 | Fritzsch | |
| 6,004,330 A | 12/1999 | Middleman et al. | |
| 6,093,185 A * | 7/2000 | Ellis | A61B 18/1477 606/28 |
| 6,162,235 A | 12/2000 | Vaitekunas | |
| 6,270,505 B1 | 8/2001 | Yoshida et al. | |
| 2004/0158261 A1* | 8/2004 | Vu | A61B 17/00234 606/114 |
| 2007/0016225 A1 | 1/2007 | Nakao | |
| 2009/0192510 A1 | 7/2009 | Bahney | |
| 2011/0184432 A1 | 7/2011 | Parihar et al. | |
| 2012/0283723 A1* | 11/2012 | Jenkins | A61B 18/14 606/41 |
| 2014/0049427 A1* | 2/2014 | Keckes | H01Q 1/3233 342/385 |
| 2014/0142567 A1* | 5/2014 | Poulsen | A61B 18/14 606/37 |
| 2014/0330285 A1 | 11/2014 | Rosenblatt et al. | |

FOREIGN PATENT DOCUMENTS

DE     202007006619     7/2007
EP     0739604     10/1996

OTHER PUBLICATIONS

International Search Report dated Dec. 19, 2016.

* cited by examiner

DEVICE FOR RECEIVING A PREPARATION IN AN EXTRACTION BAG

BACKGROUND

Field of the Invention

The invention relates to a device for receiving a preparation in an extraction bag. The preparation is detached using an electrosurgical cutting loop in a body cavity. The extraction bag is arranged at one end of an actuator which can be moved longitudinally in an insertion tube, and the extraction bag can be extended out of a distal opening of the insertion tube. In the extended state, a first bag opening of the extraction bag is held open by an elastically flexible first loop which is connected to the extraction bag, and in the retracted state, the extraction bag is closed by the first loop and covered by the distal end of the insertion tube. The electrosurgical cutting loop is designed to be elastically flexible and can be extended out of the insertion tube together with the extraction bag via the actuator in an expanding manner. The cutting loop is arranged adjacent to the first bag opening, and the electrosurgical cutting loop is arranged adjacent to the first loop.

Description of the Related Art

A device for receiving a preparation in an extraction bag is known from US 2011/0184432 A1. The extraction bag is arranged at the end of an actuator that can be longitudinally moved in an insertion tube. The extraction bag is extendable out of a central opening of the insertion tube, wherein, in the extended state, a first bag opening of the extraction bag is held open by an elastically flexible first loop to which it is connected. In the retracted state, the bag opening is closed by the first loop and covered by the distal end of the insertion tube.

It is disadvantageous in this regard that the preparation and/or detached tissue to be received has to be picked up with tongs and placed into the extraction bag. This is especially disadvantageous when the detached tissue is carcinogenic and is susceptible to being scattered in the body cavity. Moreover, when detaching the preparation using an electrosurgical cutting loop, exhaust gas, which may also be carcinogenic, can arise in the body cavity and spread unhindered in the body cavity.

For example, a device is known from DE 20 2007 006 619 U1 with an electrosurgical cutting loop that is extendable into an open position out of an opening in a hollow shaft and can be retracted in a collapsed state. In order to cut, the loop is designed as a monopolar tool through which high-frequency current can be run.

With regard to the known electrosurgical cutting loop, it is disadvantageous that it is positioned above the preparation to be resected, such as uterine tissue, and the preparation is detached by pulling closed the loop when charged with high-frequency current such that the preparation falls into the body cavity where it is picked up with tongs and placed in an extraction bag through an opening. In the case of carcinogenic tissue, this can result in undesired spreading within the body cavity.

Furthermore, U.S. Pat. No. 5,618,296 A discloses a device system in which tissue resected in a body cavity is placed into an extraction bag and shredded within the extraction bag by means of a so-called morcellator, and aspirated. A similar device system is also disclosed in U.S. Pat. No. 6,162,235 A.

These two systems also have the disadvantage that the preparation to be resected with a loop falls into the body cavity and has to be placed into the extraction bag by means of tongs.

Moreover, U.S. Pat. No. 5,190,542 A also discloses a device for receiving a preparation in an extraction bag, wherein the preparation has been detached using an electrosurgical cutting loop. The extraction bag is arranged at one end of an actuator which can be moved longitudinally in an insertion tube, and the extraction bag can be extended out of a distal opening of the insertion tube. In the extended state, a first bag opening of the extraction bag is held open by an elastically flexible first loop which is connected to the extraction bag, and in the retracted state, the extraction bag is closed by the first loop and covered by the distal end of the insertion tube. The electrosurgical cutting loop is designed to be elastically flexible and can be extended out of the insertion tube together with the extraction bag via the actuator in an expanding manner. The cutting loop is arranged adjacent to the first bag opening, wherein the electrosurgical cutting loop is also arranged adjacent to the first loop.

The present invention seeks to solve the problem of improving the known devices so as to avoid direct contact from occurring between the resected preparation and the body cavity environment. Simultaneously, it is also intended to ensure safe placement of the preparation into the extraction bag and thereby facilitate safe removal of the preparation and extraction bag.

SUMMARY

The invention relates to a device for receiving a preparation in an extraction bag. The preparation is detached using an electrosurgical cutting loop in a body cavity. The extraction bag is arranged at one end of an actuator that can be moved longitudinally in an insertion tube, and the extraction bag can be extended out of a distal opening of the insertion tube. In an extended state, a first bag opening of the extraction bag is held open by an elastically flexible first loop that is connected to the extraction bag, and, in the retracted state, the extraction bag is closed by the first loop and covered by the distal end of the insertion tube. The electrosurgical cutting loop is designed to be elastically flexible and can be extended out of the insertion tube together with the extraction bag via the actuator in an expanding manner. The cutting loop is arranged adjacent to the first bag opening, and the electrosurgical cutting loop is arranged adjacent to the first loop. The cutting loop has an exposed non-insulated electrically conductive cutting region at the distal end of the loop, and the cutting loop is insulated in an insulated region outside of the cutting region. The extraction bag has at least one second closable bag opening, and the second bag opening is arranged at the extraction bag end facing away from the first bag opening.

Because the electrosurgical cutting loop along with the extraction bag can be extended through the insertion tube and held open via the actuator, and the cutting loop is additionally arranged adjacent to the first bag opening, the cutting loop along with the bag opening can be pulled over the preparation being resected, such that when the cutting loop is pulled closed and the preparation is detached, the preparation falls directly into the extraction bag, the bag opening of which is closed by the first loop, such that any arising exhaust gas is also contained in the bag. This reliably prevents spreading of carcinogenic resected tissue and of exhaust gas inside the body cavity.

Adjacent is intended to mean directly adjacent or adjacent with only a small gap. The small gap between the electrosurgical cutting loop and the first loop makes it possible to keep the clearance width in the insertion tube relatively small for the two loops and the extraction bag. Moreover, the cutting loop can be pulled closed independently of the first loop of the bag opening, whereby the tissue is detached and the preparation falls into the extraction bag. The bag opening can then be pulled closed by the first loop.

By insulating the area outside of the cutting region, it is ensured that no cutting is possible in the rest of the insulated region—i.e. outside of the cutting region.

The second bag opening is arranged at the end of the extraction bag facing away from the first opening. The second bag opening allows a camera, for example, to be introduced into the bag for monitoring the morcellation (shredding of the resected preparation). The second bag opening can be implemented as a closable port. However, it is also possible to implement the second bag opening as a closable and/or openable port.

The electrosurgical cutting loop may be a unipolar or bipolar cutting electrode that is connectable to a high-frequency generator. The cutting electrode serves to detach and simultaneously coagulate the tissue in order to avoid bleeding. In principle, the electrosurgical cutting loop can also be implemented as a bipolar cutting electrode.

The first loop may constitute the electrosurgical cutting loop. The use of only one loop for opening and closing the bag opening, as well as resecting and/or detaching tissue, enables the insertion tube cross-section to be kept relatively small. Additionally, the structure of the device is relatively simple and cost-effective. The electrosurgical cutting loop is pulled closed simultaneously with the extraction bag attached to it, and the tissue is detached, such that the preparation remains inside the extraction bag.

The electrosurgical cutting loop may be connected to the first loop by spacers. The spacers ensure that the gap between the first loop and cutting loop does not exceed a maximum distance and that no tissue can leak out from between the loops. This additionally ensures that the bag opening is not closed before the tissue has been detached. The spacers therefore also ensure coordinated movement between the first loop and the electrosurgical cutting loop.

The first loop may be connected detachably to the extraction bag. This can be done outside of the body cavity, in particular, in order to introduce a morcellator (shredding device), for example, through the bag opening and into the bag region that has remained inside the body cavity, in order to morcellate the tissue.

The second bag opening may be closable by pulling closed a closure band arranged in the opening region. The double opening of the bag enables perforation-free introduction of both the morcellator as well as a camera. The double opening of the bag also enables the bag to be sealed against the body cavity and/or abdominal cavity. It is possible to inflate the bag for a better view. Undesired pressure loss in the extraction bag can be minimized, which may be associated with $CO_2$ savings.

The cutting loop may be connected detachably to the extraction bag. This can be done outside the body cavity to introduce a morcellator (shredding device), for example, through the bag opening and into the bag area that has remained inside the body cavity, in order to morcellate the tissue.

The extraction bag may be made of thermally-resistant material, at least in the region of the cutting loop. The insulation layer of the cutting loop also may be made of thermally-resistant material.

Polytetrafluoroethylene (PTFE) that can also be modified, or fluorinated ethylene propylene (FEP) are suitable thermally-resistant materials.

DETAILED DESCRIPTION

Figure 1:
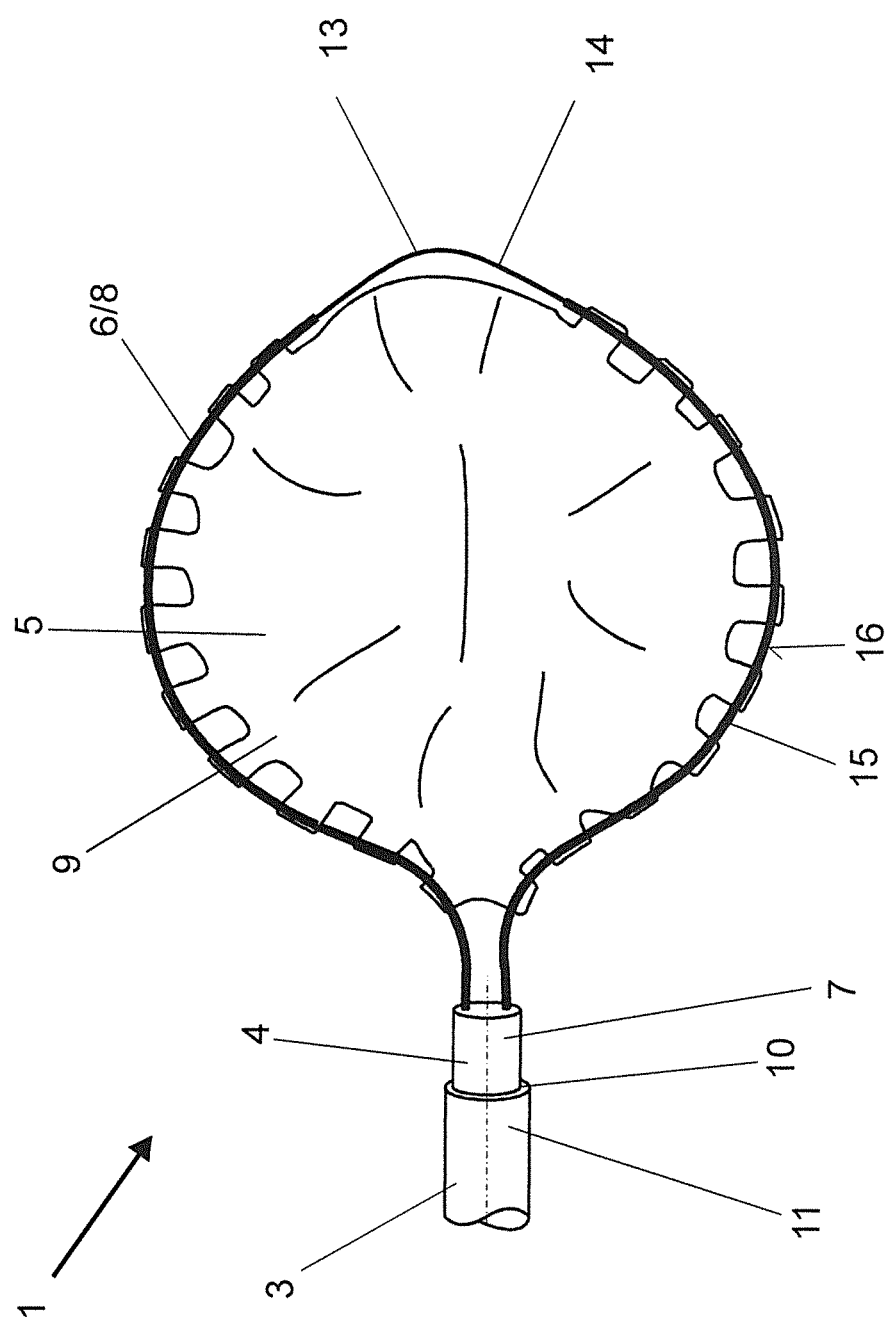
FIG. 1 a top-down view of the outline and enlarged depiction of a device for receiving a preparation in an extraction bag with extended electrosurgical cutting loop as a first loop connected to the first bag opening.

A device 1 for receiving a preparation essentially comprises an insertion tube 3, an actuator 4, an extraction bag 5 and an electrosurgical cutting loop 6.

The insertion tube 3 has the longitudinally displaceable actuator 4 in its central guide channel. An elastically flexible first loop 8 is arranged at the distal end 7 of the actuator 4, said loop being connected to a first bag opening 9 of the extraction bag 5 and serving to open the first bag opening 9 out of the distal opening 10 of the insertion tube 3 in the extended state of the distal end 7. In the still unextended, retracted state of the actuator 4, the loops 6, 8 with the extraction bag 5 are completely covered by the distal end 11 of the insertion tube 3. The first bag opening 9 is arranged at a first end 18 of the extraction bag 5 facing toward the first loop 8, 8'.

The electrosurgical cutting loop 6 is implemented as elastically flexible such that it opens in the extended state, i.e., due to its spring force. The same also applies to the first loop 8 as described above.

According to FIGS. 1 and 3 to 6, the electrosurgical cutting loop 6 is constituted by the first loop 8.

Figure 2:
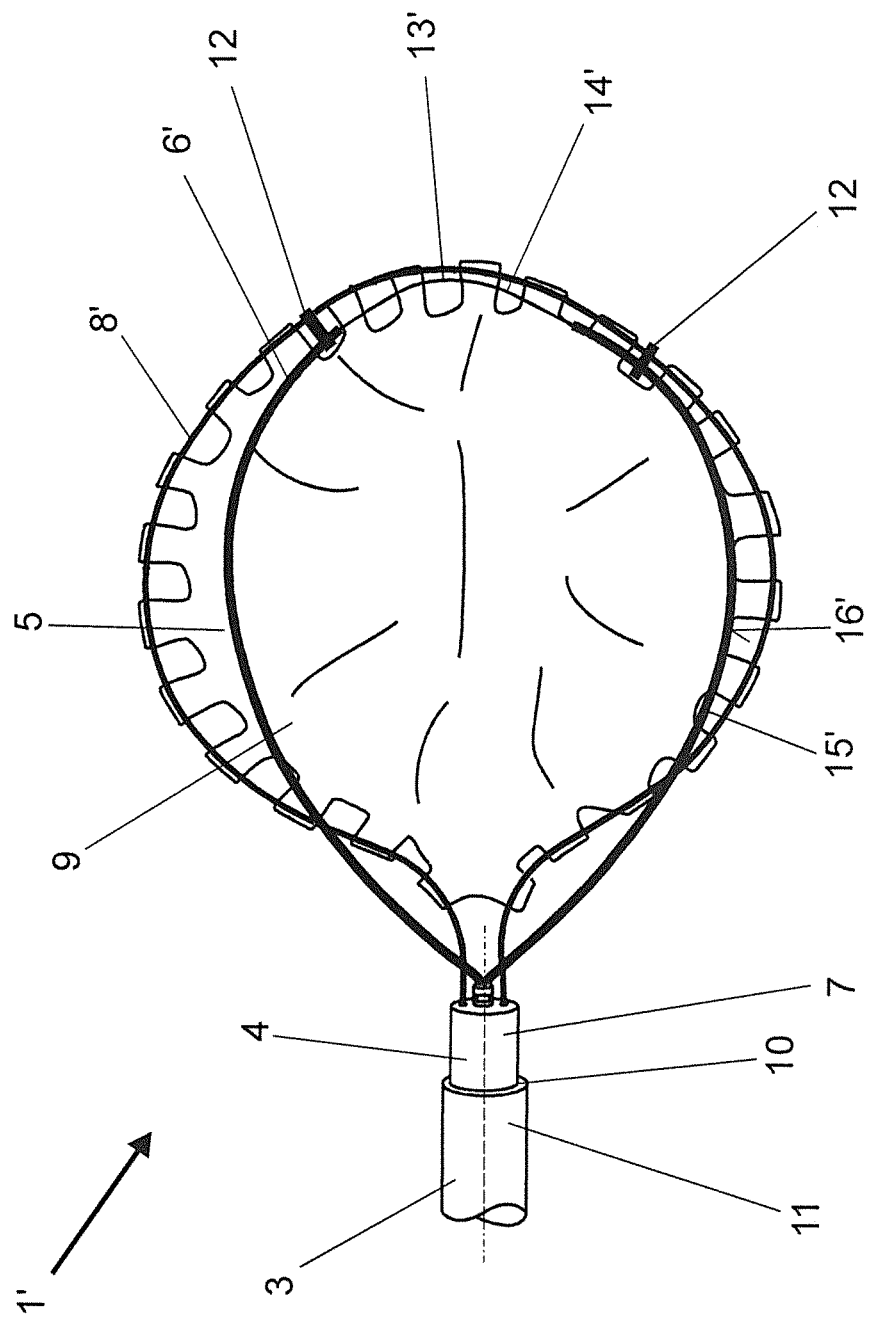
FIG. 2 a top-down view of the outline and enlarged depiction of a device for receiving a preparation in an extraction bag with extended electrosurgical cutting loop arranged adjacent to the first loop connected to the first bag opening.

According to FIG. 2, the electrosurgical cutting loop 6' is arranged adjacent to the first loop 8'. The electrosurgical cutting loop 6' is in this regard connected to the first loop 8' via the spacers 12. However, in principle, the spacers 12 can be dispensed with.

The electrosurgical cutting loop 6, 6' has at its distal end 13, 13' an exposed, uninsulated, electrically conductive cutting region 14, 14' and has, outside of the cutting region 14, 14', an insulation region 15, 15' with an insulating layer 16, 16', such as a plastic tube. In the cutting region 14, 14', the cutting loop can be more strongly curved than outside of the cutting region.

The first loop 8, 8' is detachably connected to the extraction bag 5.

According to the exemplary embodiments, the electrosurgical cutting loop 6, 6' is detachably connected to the extraction bag 5.

The extraction bag 5 has a closable second bag opening 17. According to FIGS. 4 to 6, the second bag opening 17 is arranged at the second end 19 of the extraction bag 5 facing away from the first end 18 with the first bag opening 9. The second bag opening 17 is closable by pulling closed a closure band 20 arranged in the opening region of the second bag opening 17. The second bag opening 17 can also be implemented as a closable and/or an openable port.

Figure 3:
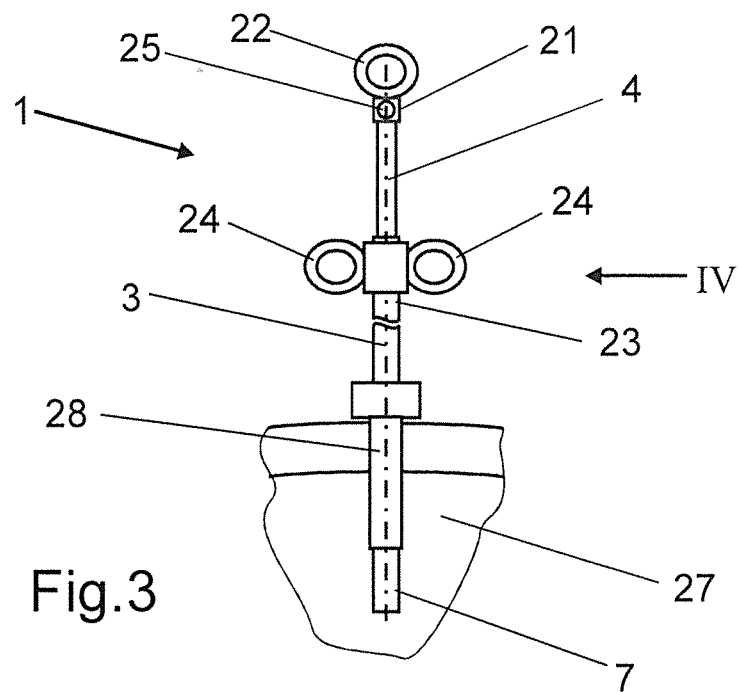
FIG. 3 a lateral view of the device from FIG. 1 in the non-extended state, being introduced into a body cavity via a trocar sleeve (in outline)
Figure 4:
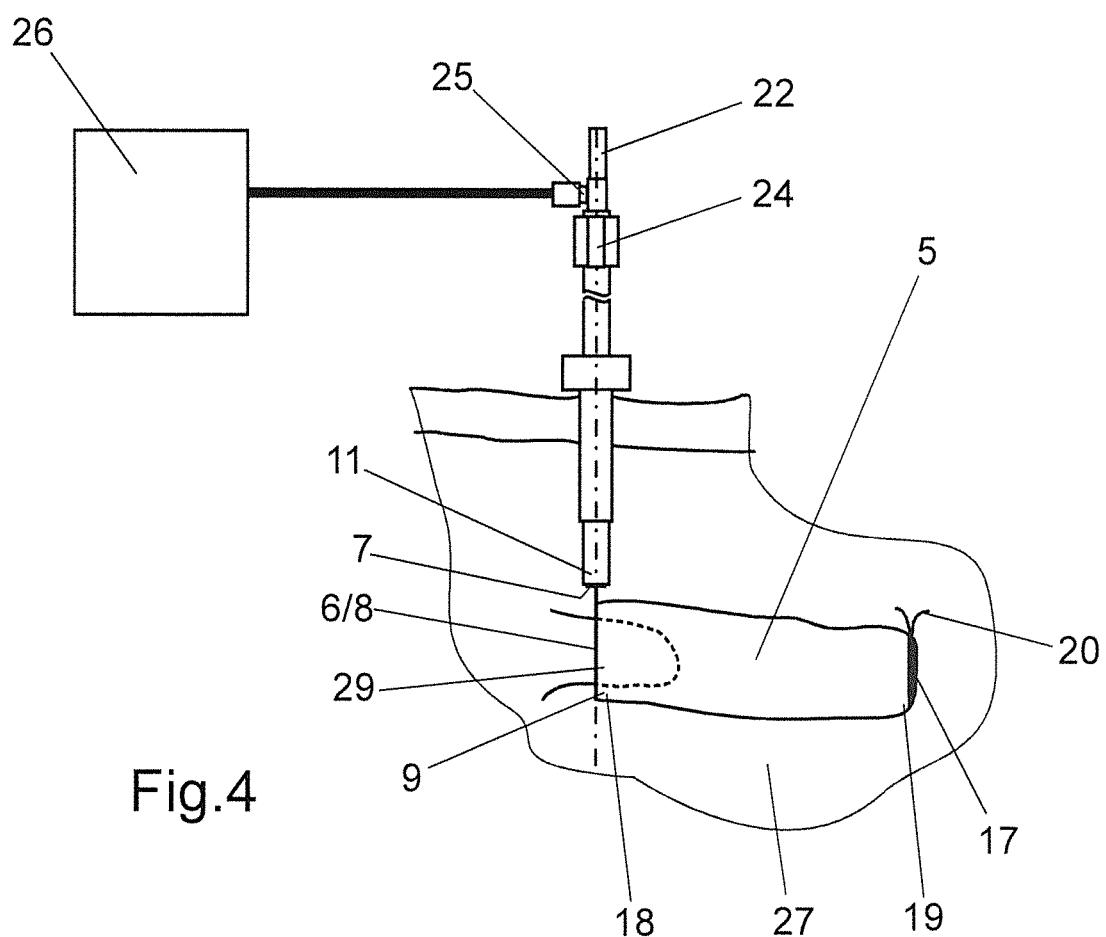
FIG. 4 a lateral view of the device from FIG. 3 from Direction IV in the extended state of the cutting loop and extraction bag with an open first bag opening placed over the preparation being resected.
Figure 6:
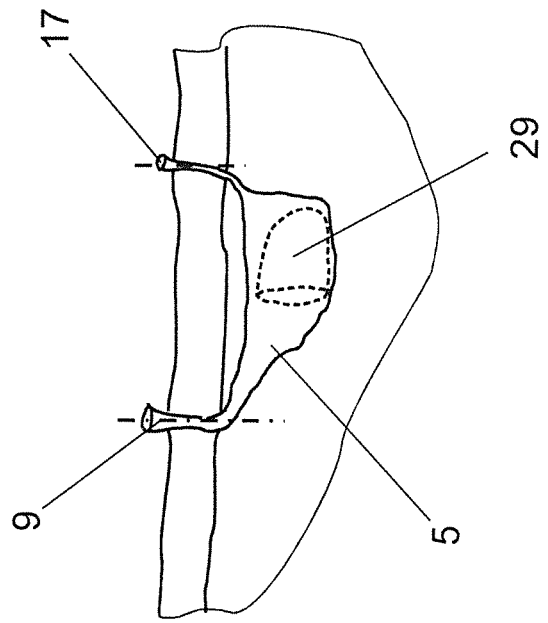
FIG. 6a lateral view of the extraction bag from FIG. 5, the ends of which have been pulled out of the body access openings for the trocar sleeves for further processing.
Figure 5:
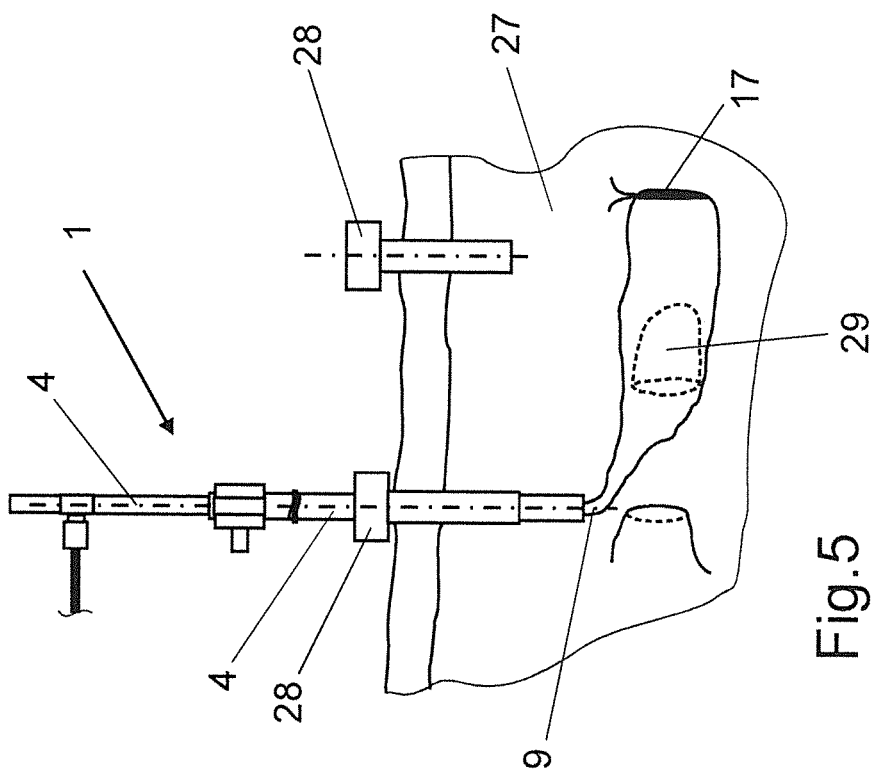
FIG. 5a lateral view of the device from FIG. 4 in the retracted state of the cutting loop and with closed first bag opening and a resected preparation in the extraction bag.

According to FIGS. 3 to 5, the actuator 4 has at its proximal end 21 a thumb ring 22 with which to effect longitudinal displacement of the actuator 4 relative to the insertion tube 3. The insertion tube 3 has at its proximal end 23 two retaining rings 24 to receive, for example, an index and middle finger.

The actuator 4, at its proximal end 21, has a high-frequency connection 25 for connection with an electrosurgical high-frequency generator 26.

To introduce the insertion tube 3 into a body cavity 27, the distal end 11 is introduced via a (laparoscopic) trocar 28, known to one skilled in the art, that has been placed in the body cavity 27. In a subsequent step, the actuator 4 is activated and extended with its distal end 7 such that the cutting loop 6 and the first loop 8 open, and the loops 6, 8 together with the first bag opening 9 are placed over the preparation 29 being resected. In an additional subsequent step, the cutting loop 6 is pulled closed, i.e., retracted with the actuator 4 into the insertion tube 3, and as a result the preparation is detached such that it falls through the first bag opening 9 into the extraction bag. Simultaneously or in a second step, the first bag opening is closed by the first loop 8. In an additional subsequent step, the first end 18 of the extraction bag 5 can be positioned outside of the body cavity 27. The second end 19 of the extraction bag 5 can be grabbed with gripping tongs (not depicted) introduced through a second trocar 28 and can also be taken out of the body cavity 27.

In additional subsequent steps, a morcellator (not depicted) can be introduced through the first bag opening 9 and a camera (not depicted), for example, can be introduced into the extraction bag 5 through the second bag opening 17. The preparation 29 can be morcellated (shredded) inside the extraction bag and removed from the body cavity 27 (contained within the bag).

Of course, the embodiments discussed in the specific description and shown in the Figures are merely illustrative exemplary embodiments of the present invention. In the light of the present disclosure a person skilled in the art has a broad spectrum of optional variations available. In particular, the relative motion between the insertion tube 3 and the actuator 4 at the proximal end 21 of the actuator 4 and at the proximal end 23 of the insertion tube 3 can be effected by grip ends (not depicted) that are displaceable relative to one another.

LIST OF REFERENCE NUMBERS 1 device
2 preparation
3 insertion tube
4 actuator
5 extraction bag
6, 6' electrosurgical cutting loop
7 distal end of 4
8, 8' first loop
9 first bag opening of 5
10 distal opening of 3
11 distal end of 3
12 Spacer
13, 13' distal end of 6, 6'
14, 14' uninsulated cutting region of 13, 13'
15, 15' insulation region of 6, 6'
16, 16' insulation layer of 15, 15'
17 second bag opening of 5
18 first end of 5
19 second end of 5
20 closure band of 17
21 proximal end of 4
22 thumb ring of 4
23 proximal end of 3
24 retaining ring of 3
25 high-frequency connection of 4
26 high-frequency generator
27 body cavity
28 trocar
29 preparation

The invention claimed is:

1. A device (1) for receiving a preparation (29) that is detached in a body cavity (27), the device (1) comprising:
    an insertion tube (3) having a distal opening (10);
    an actuator (4) that can be moved longitudinally in the insertion tube (3);
    an extraction bag (5) configured for receiving the preparation (29), the extraction bag (5) being arranged at one end (7) of the actuator (4) and being extendable out of the distal opening (10) of the insertion tube (3), thereby moving from a retracted state into an extended state, the extraction bag (5) having a first bag opening (9) and a second bag opening (17) arranged at an end of the extraction bag (5) facing away from the first bag opening (9);
    an elastically flexible first loop (8, 8') connected to the extraction bag (5) and holding the first bag opening (9) open when the extraction bag (5) is in the extended state; and
    an electrosurgical cutting loop (6, 6') arranged adjacent to the first bag opening (9) and adjacent to the first loop (8, 8'), the electrosurgical cutting loop (6, 6') having an exposed non-insulating electrically conductive cutting region (14, 14') at a distal end (13, 13') and being operative to detach the preparation (29) in the body cavity (27), the cutting loop (6, 6') further having an insulated region (15, 15') provided on the cutting loop (6, 6') outside of the cutting region (14, 14');
    wherein
    the first loop (8, 8') is detachably connected to the extraction bag (5).

2. The device of claim 1,
    wherein
    the electrosurgical cutting loop (6, 6') is a unipolar or bipolar cutting electrode and is connectable to a high-frequency generator (26).

3. The device of claim 1,
    wherein
    the second bag opening (17) is a closable port.

4. The device of claim 1,
wherein
the second bag opening (17) is an openable port.

5. The device of claim 1,
wherein
the second bag opening (17) is closable by pulling closed a closure band (20) arranged in the opening region.

6. The device of claim 1,
wherein
the cutting loop (6, 6') is detachably connected to the extraction bag (5).

7. The device of claim 1, wherein the second bag opening (17) is a camera insertion opening configured for selective insertion and withdrawal of a camera for observing the preparation (29) in the extraction bag (5).

8. The device of claim 1, wherein the electrosurgical cutting loop (6') is connected to the first loop (8') via spacers (12) extending between the first loop (8') and the insulated region (15, 15') provided on the cutting loop (6, 6') outside of the cutting region (14, 14').

9. A device (1) for receiving a preparation (29) that is detached in a body cavity (27), the device (1) comprising:
an insertion tube (3) having a distal opening (10);
an actuator (4) that can be moved longitudinally in the insertion tube (3);
an extraction bag (5) configured for receiving the preparation (29), the extraction bag (5) being arranged at one end (7) of the actuator (4) and being extendable out of the distal opening (10) of the insertion tube (3), thereby moving from a retracted state into an extended state, the extraction bag (5) having a first bag opening (9) and a second bag opening (17) arranged at an end of the extraction bag (5) facing away from the first bag opening (9);
an elastically flexible first loop (8, 8') connected to the extraction bag (5) and holding the first bag opening (9) open when the extraction bag (5) is in the extended state; and
an electrosurgical cutting loop (6, 6') arranged adjacent to the first bag opening (9) and adjacent to the first loop (8, 8'), the electrosurgical cutting loop (6, 6') having an exposed non-insulating electrically conductive cutting region (14, 14') at a distal end (13, 13') and being operative to detach the preparation (29) in the body cavity (27), the cutting loop (6, 6') further having an insulated region (15, 15') provided on the cutting loop (6, 6') outside of the cutting region (14, 14');
wherein
the extraction bag (5) is made of a thermally resistant material, at least in the region of the cutting loop (6, 6').

10. The device of claim 9,
wherein
the insulation region (15, 15') of the cutting loop (6, 6') has an insulation layer (16, 16') made of a thermally resistant material.

11. The device claim 9,
wherein
the thermally resistant material is a polytetrafluoroethylene.

12. The device claim 9,
wherein
the thermally resistant material is a fluorinated ethylene propylene.

13. The device of claim 9, wherein the electrosurgical cutting loop (6') is connected to the first loop (8') via spacers (12), the spacers (12) extend between the first loop (8') and the insulated region (15, 15') provided on the cutting loop (6, 6') outside of the cutting region (14, 14').

14. The device of claim 9, wherein the second bag opening (17) includes closing means (20) for selectively opening and closing the second bag opening (17).

15. The device of claim 14, wherein the closing means (20) is a closure band (20) for selectively opening and closing the second bag opening (17).

* * * * *